United States Patent
Avery

(10) Patent No.: US 10,130,558 B2
(45) Date of Patent: Nov. 20, 2018

(54) CODED COLLAPSIBLE DRUG RESERVOIR

(75) Inventor: Richard James Vincent Avery, Chipping Campden (GB)

(73) Assignee: Sanofi-Aventis Deutschland GmbH, Frankfurt am Main (DE)

(*) Notice: Subject to any disclaimer, the term of this patent is extended or adjusted under 35 U.S.C. 154(b) by 1131 days.

(21) Appl. No.: 13/519,233

(22) PCT Filed: Jan. 21, 2011

(86) PCT No.: PCT/EP2011/050798
§ 371 (c)(1),
(2), (4) Date: Dec. 7, 2012

(87) PCT Pub. No.: WO2011/089206
PCT Pub. Date: Jul. 28, 2011

(65) Prior Publication Data
US 2013/0072878 A1    Mar. 21, 2013

Related U.S. Application Data

(60) Provisional application No. 61/297,608, filed on Jan. 22, 2010.

(30) Foreign Application Priority Data

Apr. 23, 2010   (EP) .................................. 10160871

(51) Int. Cl.
*A61J 1/06*   (2006.01)
*A61M 5/28*   (2006.01)
(Continued)

(52) U.S. Cl.
CPC ................. *A61J 1/067* (2013.01); *A61J 1/06* (2013.01); *A61J 1/062* (2013.01); *A61J 1/10* (2013.01);
(Continued)

(58) Field of Classification Search
CPC ...... A61J 2205/40; A61J 2205/60; A61J 1/06; A61J 1/062; A61J 1/067; A61J 1/10;
(Continued)

(56) References Cited

U.S. PATENT DOCUMENTS 533,575 A    2/1895   Wilkens
4,836,397 A    6/1989   Fowles
(Continued)

FOREIGN PATENT DOCUMENTS

EP    0937471 A2    8/1999
EP    0937476 A2    8/1999
(Continued)

OTHER PUBLICATIONS

Extended European Search Report issued in European Patent Application No. 10160871.9 dated Oct. 25, 2010.
(Continued)

*Primary Examiner* — Shefali Patel
(74) *Attorney, Agent, or Firm* — McCarter & English, LLP

(57) ABSTRACT

A coded collapsible drug reservoir and a drug delivery system including the coded collapsible drug reservoir. The drug reservoir includes a collapsible housing and a port in communication with the collapsible housing. The drug reservoir further includes a coding feature disposed on the drug reservoir, and the coding feature identifies the drug reservoir.

20 Claims, 7 Drawing Sheets

(51) Int. Cl.
*A61J 1/10* (2006.01)
*A61M 5/24* (2006.01)
*A61M 5/315* (2006.01)
*A61M 5/31* (2006.01)

(52) U.S. Cl.
CPC ............ *A61M 5/28* (2013.01); *A61J 2205/00* (2013.01); *A61J 2205/40* (2013.01); *A61J 2205/60* (2013.01); *A61M 5/2425* (2013.01); *A61M 5/3129* (2013.01); *A61M 5/31525* (2013.01); *A61M 5/31533* (2013.01); *A61M 2005/2403* (2013.01); *A61M 2205/19* (2013.01); *A61M 2205/27* (2013.01); *A61M 2205/276* (2013.01); *A61M 2205/60* (2013.01); *A61M 2205/6009* (2013.01); *A61M 2205/6036* (2013.01); *A61M 2205/6045* (2013.01)

(58) Field of Classification Search
CPC ...... A61J 1/16; A61J 2205/00; A61J 2205/10; A61J 2205/20; A61M 2205/6045; A61M 2205/6063; A61M 2005/2403; A61M 5/2425; A61M 5/282; A61M 2205/276; A61M 2205/582; A61M 2205/60; A61M 2205/6009; A61M 2205/6072; A61M 5/28; A61M 5/3129; A61M 2205/12; A61M 2205/121; A61M 2205/123; A61M 2205/19; A61M 2205/27; A61M 2205/6036; A61M 2205/6054; A61M 2205/6081

See application file for complete search history.

(56) References Cited

U.S. PATENT DOCUMENTS

| | | | |
|---|---|---|---|
| 5,226,895 A | 7/1993 | Harris | |
| 5,279,586 A | 1/1994 | Balkwill | |
| 5,304,152 A | 4/1994 | Sams | |
| 5,320,609 A | 6/1994 | Haber et al. | |
| 5,383,865 A | 1/1995 | Michel | |
| 5,480,387 A | 1/1996 | Gabriel et al. | |
| 5,505,704 A | 4/1996 | Pawelka et al. | |
| 5,582,598 A | 12/1996 | Chanoch | |
| 5,626,566 A | 5/1997 | Petersen et al. | |
| 5,674,204 A | 10/1997 | Chanoch | |
| 5,688,251 A | 11/1997 | Chanoch | |
| 5,921,966 A | 7/1999 | Bendek et al. | |
| 5,961,495 A | 10/1999 | Walters et al. | |
| 5,971,972 A * | 10/1999 | Rosenbaum | A61J 1/10 604/411 |
| 5,980,501 A | 11/1999 | Gray | |
| 6,004,297 A | 12/1999 | Steenfeldt-Jensen et al. | |
| 6,193,698 B1 | 2/2001 | Kirchhofer et al. | |
| 6,221,046 B1 | 4/2001 | Burroughs et al. | |
| 6,235,004 B1 | 5/2001 | Steenfeldt-Jensen et al. | |
| 6,248,095 B1 | 6/2001 | Giambattista et al. | |
| 6,648,859 B2 * | 11/2003 | Bitdinger | A61M 5/24 604/218 |
| 6,899,698 B2 | 5/2005 | Sams | |
| 6,936,032 B1 | 8/2005 | Bush, Jr. et al. | |
| 7,241,278 B2 | 7/2007 | Moller | |
| 8,177,767 B2 | 5/2012 | Kristensen et al. | |
| 8,597,257 B2 | 12/2013 | Modi | |
| 8,632,506 B2 | 1/2014 | Steenfeldt-Jensen et al. | |
| 2002/0052578 A1 | 5/2002 | Moller | |
| 2002/0120235 A1 | 8/2002 | Enggaard | |
| 2003/0004466 A1 | 1/2003 | Bitdinger et al. | |
| 2003/0050609 A1 | 3/2003 | Sams | |
| 2003/0072676 A1 * | 4/2003 | Fletcher-Haynes | A61J 1/10 422/23 |
| 2004/0059299 A1 | 3/2004 | Moller | |
| 2004/0210199 A1 | 10/2004 | Atterbury et al. | |
| 2004/0267207 A1 | 12/2004 | Veasey et al. | |
| 2005/0113765 A1 | 5/2005 | Veasey et al. | |
| 2006/0153693 A1 | 7/2006 | Fiechter et al. | |
| 2007/0191780 A1 * | 8/2007 | Modi | A61M 5/282 604/187 |
| 2007/0213684 A1 * | 9/2007 | Hickle | A61J 1/14 604/500 |
| 2009/0275916 A1 | 11/2009 | Harms et al. | |

FOREIGN PATENT DOCUMENTS

| | | | |
|---|---|---|---|
| JP | 2004538118 A | 12/2004 | |
| JP | 2006314815 A | 11/2006 | |
| JP | 2009526575 A | 7/2009 | |
| JP | 2009540995 A | 11/2009 | |
| WO | 9938554 A1 | 8/1999 | |
| WO | 0110484 A1 | 2/2001 | |
| WO | 03026724 A1 | 4/2003 | |
| WO | 33026724 A1 | 4/2003 | |
| WO | WO 2008000827 A1 * | 1/2008 | .............. A61M 5/24 |

OTHER PUBLICATIONS

English Translation of Decision of Rejection issued in Japanese Patent Application No. 2012-549364 dated Jun. 9, 2015.
International Preliminary Report on Patentability for Int. App. No. PCT/EP2011/050798, dated Aug. 2, 2012.
Form PCT/ISA/220, Notification of Transmittal of the International Search Report and the Written Opinion of the International Searching Authority, or the Declaration issued in International Patent Application No. PCT/EP2011/050798 dated Jul. 21, 2011.

* cited by examiner

CODED COLLAPSIBLE DRUG RESERVOIR

CROSS REFERENCE TO RELATED APPLICATIONS

The present application is a 35 U.S.C. 371 National Application of PCT/EP2011/050798 filed Jan. 21, 2011, which claims priority to U.S. Provisional Patent Application No. 61/297,608 filed Jan. 22, 2010 and European Patent Application No. 10160871.9 filed Apr. 23, 2010, the entire contents of which are incorporated entirely herein by reference.

FIELD OF THE PRESENT DISCLOSURE

Specific embodiments of this disclosure relate to reservoirs, particularly reservoirs containing a medicament. More particularly, the present disclosure is generally directed to a collapsible drug reservoir, which may beneficially prevent reservoir use with an incorrect drug delivery device and which may be provided with certain coding features. As just one example, such medicament reservoirs may comprise a collapsible ampoule, cartridge, vial, or pouch, and may be used with a suitable medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient may load a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder may be disconnected from the drug delivery device and the empty cartridge may be removed and replaced with a new cartridge. Most suppliers of such cartridges recommend that the user disposes of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user may simply load a new cartridge into the delivery system without the drug delivery device or without the cartridge having any mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short-acting insulin in lieu of a long-acting insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness. This is a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament. However, these cartridges may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate, mechanically code, or electronically code a cartridge to its drug type and to design an injection device that accepts or works with the dedication or coded features provided on or with the cartridge so as to prevent unwanted cartridge cross use. Similarly, there is also a general need for a dedicated cartridge that allows the medical delivery device to be used with an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e. making it more difficult for counterfeiters to provide unregulated counterfeit medicament carrying products.

Problem to be Solved

The problem to be solved by the present invention is to provide a drug reservoir and a drug delivery system where the safety for the user is improved.

SUMMARY

One aspect of the present disclosure relates to a drug reservoir. The drug reservoir may be adapted for use with a drug delivery device. The drug reservoir may be collapsible. In particular, the drug reservoir may comprise a collapsible housing. This collapsible housing preferably stores a medicament, in particular one or a plurality of doses of the medicament. The medicament may have at least one drug agent. For example, the collapsible housing may be deformed when force is exerted on it, e.g. when the medicament is forced out of the housing. This may facilitate delivering the medicament from the reservoir. The collapsible drug reservoir may comprise a coding feature. The coding feature may be disposed on, along or in the reservoir, for example. The coding feature may be configured to code information related to the drug reservoir such that reading the code may help to identify the specific drug reservoir, in particular information related to the drug reservoir. In particular, the coding feature may serve for identifying the drug reservoir and, therefore, the medicament contained in the reservoir. The coding feature may prevent use of the drug reservoir with an incorrect drug delivery device.

According to an embodiment, a shape of the reservoir is configured to act as the coding feature. In particular, the shape of the collapsible housing may be configured to act as a coding feature identifying the medicament contained in the reservoir. According to an embodiment, the collapsible housing comprises a generally cylindrical structure. Alternatively, the collapsible housing may comprise a generally oval-shaped structure. Alternatively, the collapsible housing may comprise a triangular-shaped structure. Alternatively, the collapsible housing may comprise a trapezoidal-shaped top surface. A given shape or structure of the collapsible housing and/or its surface may identify a predetermined medicament held in the collapsible housing, for example. Furthermore, the given shape or structure may prevent the reservoir from being inserted into an incorrect device.

According to an embodiment, the drug reservoir further includes a port. The port may be adapted and arranged for fluid communication with the collapsible housing. In particular, this port may serve as an exit port from which the medicament stored in the collapsible housing may exit the housing. The coding feature may be located on the port, for example. The coding feature may comprise at least one of an indentation or a protrusion on the port.

The port may comprise a hub for attaching a needle, for example. Alternatively, the port may comprise a septum. The septum may be adapted and arranged to seal the port fluid-tightly. In particular, the septum may be configured to prevent flow of the medicament out of the collapsible housing. Alternatively, the port may comprise a tube. The tube may be configured to attach to at least one of a septum and a needle hub, for example. In particular, the tube may connect the port with one of the needle hub and the septum. Additionally or alternatively, the port may comprise a support ring. The support ring may be arranged circumferentially around the port. The support ring may comprise a stiff element. In particular, the support ring may be stiffer than the flexible housing and/or the port. The support ring may be configured to prevent the port from collapsing. The support ring may comprise the coding feature, for example.

According to an embodiment, the coding feature comprises a mechanical coding feature. The mechanical coding feature may be configured to cooperate with a corresponding, in particular mating, coding feature provided by the drug delivery device using the reservoir. The coding feature of the reservoir may comprise at least one of a recessed or raised feature. In particular, the coding feature may comprise an embossed feature, a hole or an indentation of the reservoir. For example, the coding feature may comprise a protrusion. In this case, the mating coding feature may comprise an indentation. For example, the mating coding feature may be arranged on an inner surface of a reservoir holder or a housing part of the device. Mechanical cooperation of the coding feature and the mating coding feature may help to prevent insertion of a reservoir having the wrong coding feature and, thus, as an example, holding a wrong type of medicament into the device. User safety may be increased in this way.

According to an embodiment, the coding feature is a coding feature configured to be electronically detectable. The electronically detectable coding feature may be detected when the reservoir is inserted into the drug delivery device, for example. In this way, a user may realize at once which medicament is contained in the reservoir.

According to an embodiment, the reservoir comprises a non-collapsible feature. The non-collapsible feature may be connected to the collapsible housing. The non-collapsible feature may comprise the coding feature. The non-collapsible feature may be a stiff element, for example. In particular, the non-collapsible feature may be stiffer than the collapsible housing. The coding element may comprise a coding plate, for example, or the previously mentioned support ring. The coding plate may be fixed to the reservoir. The coding plate may be preferably a stiff element. The coding plate may comprise one or a plurality of coding features.

According to an embodiment, the coding feature is provided on an outer edge of the reservoir. The outer edge may comprise a sealing means of the reservoir. In particular, the sealing means may seal the reservoir fluid-tightly such that medicament is prevented to leak from the outer edge of the reservoir.

According to an embodiment, the collapsible housing comprises a plurality of sheets of sheet material. The sheet material may be adapted to form the collapsible housing. The plurality of sheets may be sealed together. Preferably, the sheet material comprises several layers of material. The sheet material may comprise laminated material. The sheet material may provide at least one of a long-term chemical compatibility with a given drug or medicament and a barrier to air.

According to an embodiment, the collapsible housing is constructed from a single sheet of sheet material. The sheet material may be folded and crimped together to form the collapsible housing.

A further aspect relates to a drug delivery system. The drug delivery system may comprise a drug delivery device, e.g. a pen-type device, for example a pen-type injector. The drug delivery system may be configured to deliver a medicament. The drug delivery system may comprise a housing. The housing may receive the previously described drug reservoir. The housing may contain a dose setter. The dose setter may be operably connected to the reservoir. The drug delivery system may further include a dose button. The dose button may be operably connected to the reservoir of medicament. The dose button may be capable of being depressed by a user of the drug delivery system. A user may use the drug delivery system to deliver (e.g., by injecting) medicament that is stored in the coded collapsible drug reservoir.

According to an embodiment, the drug delivery system may comprise a dispensing mechanism. The dispensing mechanism may be configured for dispensing the medicament from the reservoir. In particular, the dispensing mechanism may be activated when the user depresses the dose button. The dispensing mechanism may provide at least one of a suction force, a compression force, and a sacrificial fluid in order to dispense medicament from the reservoir. For example, upon activating the dispensing mechanism, a compression force may be applied onto the collapsible housing such that medicament is forced out of the housing.

According to an embodiment, the device comprises a device coding feature. The device coding feature may be adapted and arranged to mechanically or electrically cooperate with the coding feature of the reservoir when the reservoir is connected to the device. Cooperation of the coding feature of the reservoir and the device coding feature may be configured to prevent use of the device with a non-mating reservoir. In particular, mechanical cooperation of the coding feature and the device coding feature may prevent that a reservoir holding a wrong medicament is inserted into the device. Thus, dispensing of a wrong type of medicament from the device may be prevented.

According to a preferred embodiment, a drug reservoir is provided which is adapted for use with a drug delivery device, the drug reservoir comprising a collapsible housing and a coding feature, wherein said coding feature is configured to code information related to the drug reservoir.

According to a preferred embodiment, a drug reservoir is provided comprising a collapsible housing, a port in communication with the collapsible housing, and a coding feature disposed on the drug reservoir, wherein said coding feature identifies the drug reservoir.

According to a preferred embodiment, a drug delivery system is provided to deliver medicament, the drug delivery system comprising a housing containing a dose setter operably connected to a reservoir of medicament containing at least one drug agent, wherein the reservoir comprises a collapsible housing, a port in communication with the collapsible housing, and a coding feature disposed on the drug reservoir, wherein said coding feature identifies the drug reservoir. The drug delivery system further comprises a dose button operably connected to the reservoir of medicament, wherein the dose button is capable of being depressed by a user of the drug delivery system.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
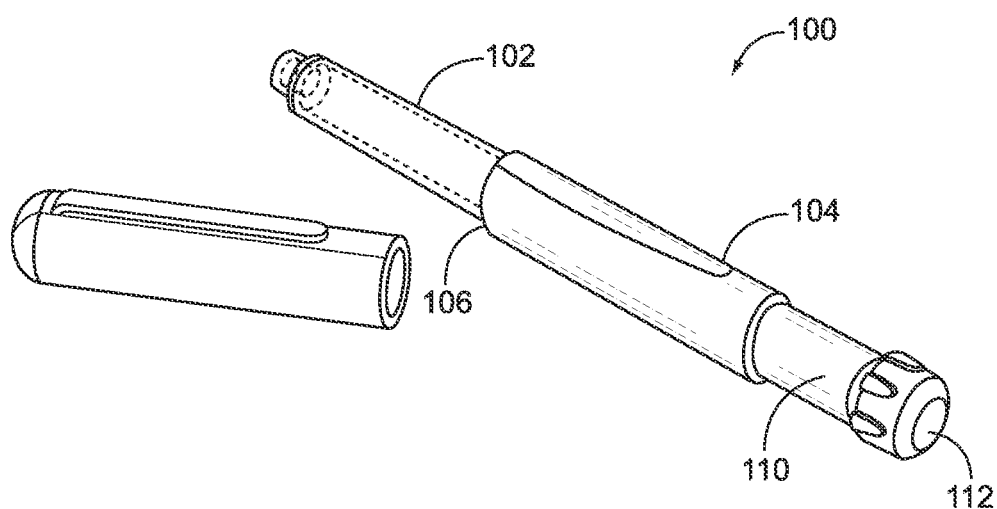
FIG. 1 illustrates a typical pen type drug delivery device that may be used in an exemplary embodiment.

Referring first to FIG. 1, there is shown a typical drug delivery device 100 in accordance with one embodiment. Drug delivery device 100 may be used for administering or injecting a medicament. The drug delivery device 100 includes a housing 104, 102 having a first reservoir retaining part 102 and a second main (exterior) housing part 104. A first end of the reservoir retaining part 102 and a second end of the main housing 104 are secured together by retaining features 106. In this illustrated arrangement, the reservoir retaining part 102 is secured within the second end of the main housing 104.

A reservoir from which a number of doses of a medicinal product may be dispensed is provided in the reservoir retaining part 102. Preferably, the reservoir contains a type of medicament that must be administered often, such as once or more times a day. One such medicament may be insulin, for example.

Drug delivery device 100 also includes a dose setting mechanism 110. This dose setting mechanism may include a dose button 112. A user of the drug delivery device 100 may use the dose setting mechanism 110 in order to set and deliver a dose of medicament from the reservoir provided in the reservoir retaining part 102. The dose setting mechanism 110 may operate in ways known in the art or later developed. The pen type syringe may comprise a re-usable or a disposable pen type syringe. Where the syringe comprises a re-usable device, the cartridge holder or reservoir retaining part 102 and the dose setting mechanism 110 may be removably coupled together. In a disposable device, they may be permanently coupled together.

The disclosed drug reservoir (see, for example, drug reservoir 200 in FIG. 2) is a collapsible drug reservoir. The drug reservoir may be coded for use with a suitable drug delivery device. For instance, the coded collapsible drug reservoir could be used with drug delivery device 100. The coded collapsible drug reservoir is preferably designed for use with a reusable drug delivery device. As is known in the art, in a reusable drug delivery device, the drug reservoir (e.g., cartridge) is removable and replaceable. The coded collapsible drug reservoir may also be designed for use with a disposable drug delivery device.

The coded collapsible drug reservoir may offer numerous advantages over typical drug reservoirs. For example, the proposed collapsible reservoirs may be less expensive, more compact, and/or less fragile than typical drug reservoirs such as those typical drug reservoirs comprising a glass cartridge. Further, the coding may ensure that particular drugs are only used in the correct drug delivery device.

The coded collapsible drug reservoir may include a collapsible housing, and this collapsible housing preferably stores a medicament, preferably a plurality of doses of the medicament. The coded collapsible drug reservoir may further include a port that may be in fluid communication with the collapsible housing and hence the medicament contained within this housing. This port may serve as an exit port from which the medicament stored in the collapsible housing may exit the housing. Still further, the coded collapsible drug reservoir may include a coding feature disposed on, along, or in the drug reservoir. Among other things, this coding feature may serve to identify the drug reservoir and, hence, the medicament contained within the drug reservoir.

Beneficially, this coding feature may ensure that drugs are only used in the correct drug delivery device and/or that drug delivery devices can react to a drug in a correct or intended manner. Specifically, the disclosed reservoir and drug delivery system can help a user distinguish between medicaments, thereby ensuring that a delivery device can only be used with a medicament for which it is intended. Therefore, with the coded collapsible drug reservoir, a user may be prevented from loading an incorrect drug reservoir into a given delivery device due to a coding feature of the incorrect reservoir that is not intended for the given device. Accordingly, the user may be prevented from completing one or more of the following actions: fully inserting an incorrect reservoir into a reservoir holder, or attaching an incorrect reservoir and/or reservoir holder into a medical delivery device or medical delivery system.

Coded collapsible drug reservoirs in accordance with exemplary embodiments will be further described with reference to FIGS. 2-4. For example, FIGS. 2(A)-(F) depict various examples of coded collapsible drug reservoirs. In particular, FIGS. 2(A)-(F) each depict coded collapsible drug reservoirs 200, 220, 240, 260, 280, and 290, respectively.

Figure 2A:
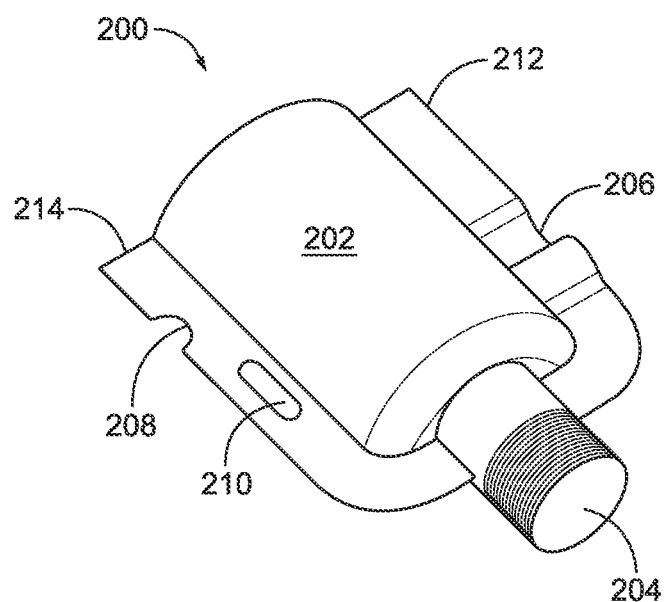
FIGS. 2(A)-(F) illustrate perspective views of examples of coded collapsible drug reservoirs, in accordance with exemplary embodiments.
Figure 2B:
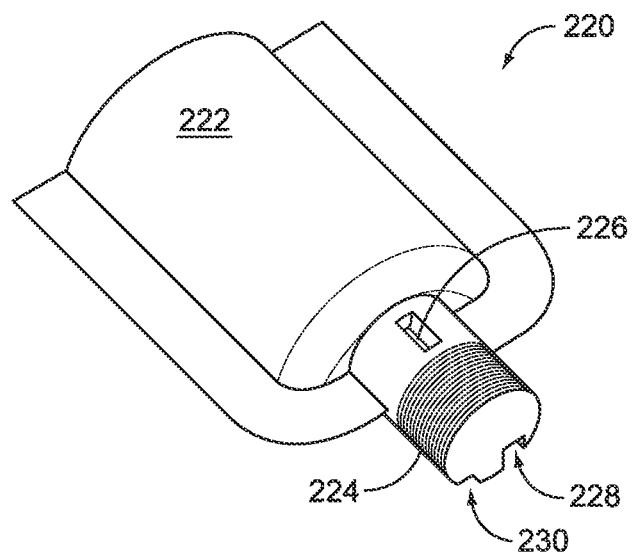
Figure 2C:
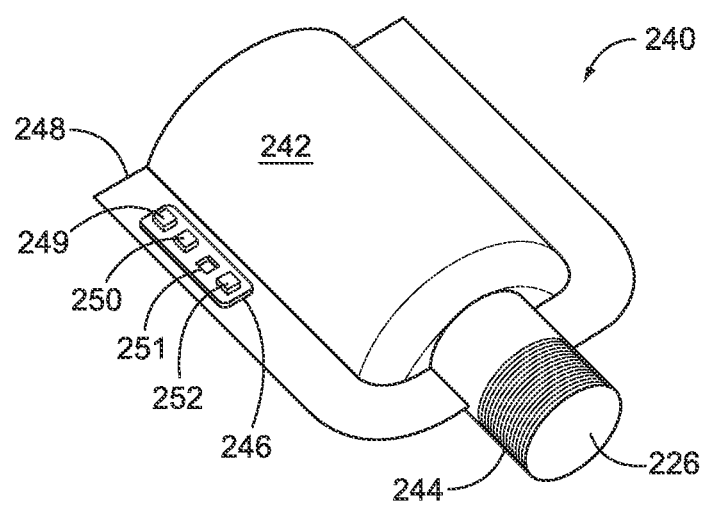
Figure 2D:
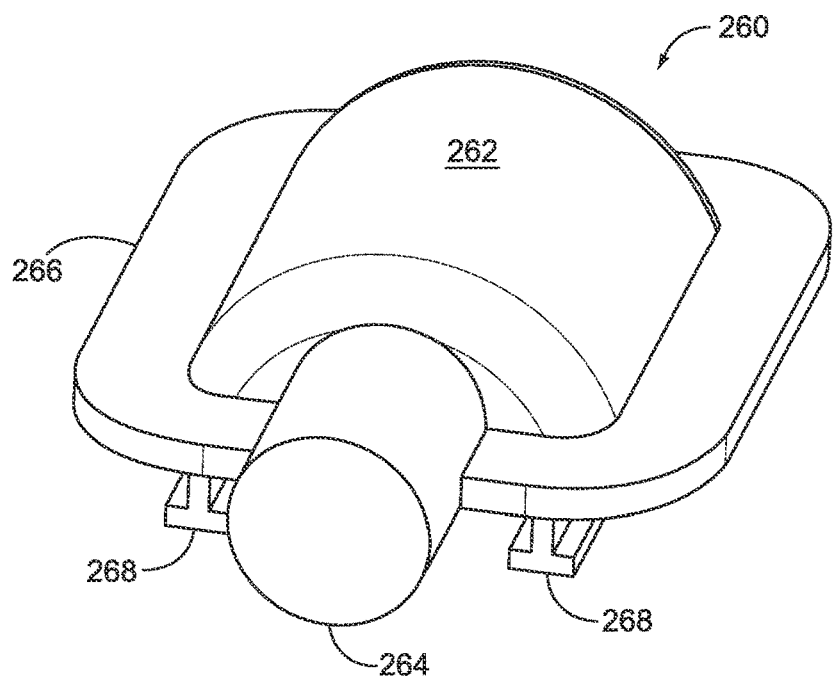
Figure 2E:
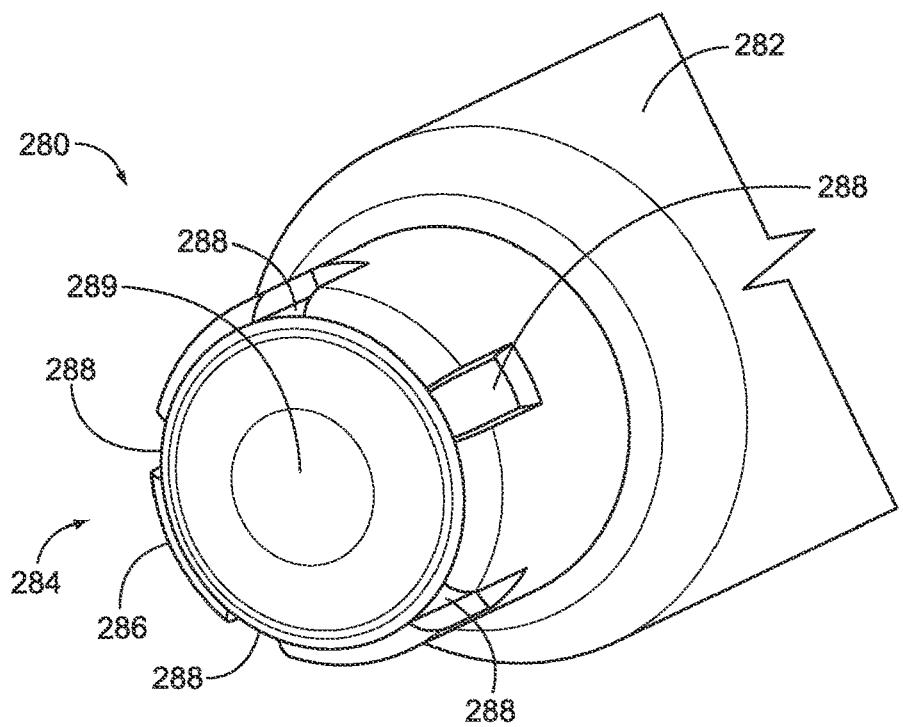
Figure 2F:
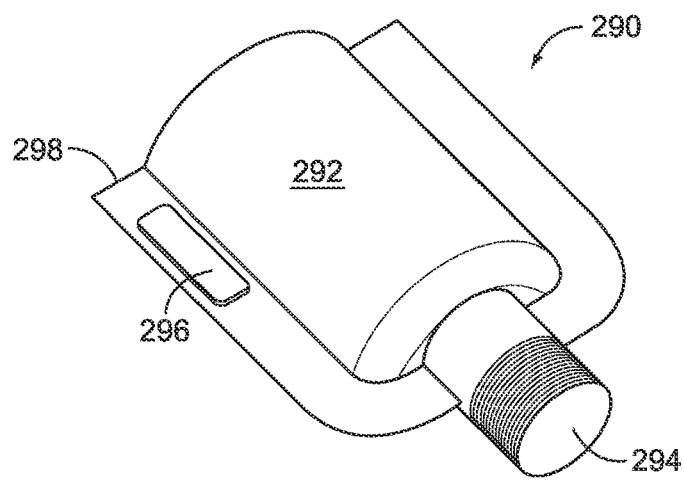

As shown, each of these drug reservoirs includes a collapsible housing portion and a port in communication with the collapsible housing. Specifically, as shown in FIG. 2(A), coded collapsible drug reservoir 200 includes collapsible housing 202 and port 204 in communication with collapsible housing 202. As shown in FIG. 2(B), coded collapsible drug reservoir 220 includes collapsible housing 222 and port 224 in communication with collapsible housing 222. As shown in FIG. 2(C), coded collapsible drug reservoir 240 includes collapsible housing 242 and port 244 in communication with collapsible housing 242. As shown in FIG. 2(D), coded collapsible drug reservoir 260 includes collapsible housing 262 and port 264 in communication with collapsible housing 262. As shown in FIG. 2(E), coded collapsible drug reservoir 280 includes collapsible housing 282 and port 284 in communication with collapsible housing 282. Finally, as shown in FIG. 2(F), coded collapsible drug reservoir 290 includes collapsible housing 292 and port 294 in communication with collapsible housing 292.

The collapsible housings depicted in these figures may be composed of various materials that result in a collapsible structure. Examples of possible materials include polymers such as PET, PE, PVC, or PP, or foils such as aluminium. These housings may be formed from, for example, sheet material. The sheet material may be manipulated as necessary (e.g., folded and crimped (i.e., sealed at the edges)) in order to form a collapsible housing of a desired shape and size. The sheet material may comprise several layers or be of a laminated construction in order to meet various desired requirements. For example, desired requirements may include long-term chemical compatibility with a particular drug, a barrier to air, desired strength, and desired sealing capability.

Returning to FIGS. 2(A)-(F), each of these drug reservoirs include a coding feature disposed on or along the drug reservoir. Each of these coding features may serve to identify information related to the particular drug reservoir the coding feature is disposed on. For instance, each coding feature may serve to identify the particular medicament that is stored in the coded collapsible drug reservoir. The type of coding feature for the collapsible drug reservoir may vary. It should be understood that these coding features depicted in FIGS. 2(A)-(F) are intended as examples of possible coding features in accordance with the disclosed coded reservoir. Other types of coding features are possible.

In an embodiment, the coding feature on a coded collapsible drug reservoir may be a mechanical coding feature. For instance, the coding may be coding by number of features, size, shape, position, asymmetry, coding by more than one dimension/feature, and/or color. Such a mechanical coding feature may cooperate with a corresponding coding feature on a drug delivery device, such as drug delivery device 100. Preferably, the mechanical coding feature is disposed on the drug reservoir. Such mechanical coding features will be described in greater detail below, with particular reference to FIGS. 2(A)-(E). Alternatively, the shape of the reservoir itself may serve as the coding feature that identifies the drug reservoir. In another embodiment, the coding feature on a collapsible drug reservoir may be a coding feature that may be detected electronically.

In addition to various possible types of features, these coding features for a collapsible drug reservoir may be located at various positions on or along the drug reservoir. For instance, the coding feature may be located on the port of the drug reservoir, a sidewall of the reservoir, a sealing means of the reservoir, the collapsible housing, an edge of the collapsible housing, and/or other locations. Various possible locations will be described with reference to FIGS. 2(A)-(F). However, it should be understood that the coding features may be located in other possible positions as well.

As particular examples, the coding features may be embossed or debossed features, holes, or indentations on an outer edge of the drug reservoir. Such features are depicted in FIG. 2(A). In FIG. 2(A), the collapsible reservoir 200 comprises a plurality of coding features 206, 208, and 210. In this arrangement, coded feature 206 is located on a first outer edge 212 of the reservoir 200, and the coded features 208 and 210 are located on a second outer edge 214 of the reservoir 200. These outer edges may be the crimp (i.e., sealing means) of the collapsible housing 202.

In an alternative arrangement, the coding features may comprise indentations and/or protrusions on the port of the coded collapsible drug reservoir. These indentations or protrusions may be orientated in practically any direction. For example, such indentations and/or protrusions may be oriented in the axial and/or traverse direction. The particular indentations or protrusions may depend on how the reservoir is intended to be attached to an intended drug delivery device. An example of such coding features is shown in FIG. 2(B). Reservoir 220 includes coding features 226, 228, and 230. As shown, these features are indentations in the port 224. The particular indentation arrangement shown may allow the reservoir 220 to only be connected to a given drug delivery device 100 that is designed to only accept certain collapsible reservoirs comprising ports of this given indentation geometry. Of course, those of skill in the art will recognize alternative indentation and/protrusion arrangements may also be used and configured to prevent unwanted reservoir cross-use.

As another example, the coding feature for the collapsible reservoir may comprise a coding plate that is fixed to some point on the reservoir. An example of a coding plate is shown in FIG. 2(C). In FIG. 2(C), the reservoir 240 comprises a coding plate 246 and this coding plate 246 is positioned near an outer edge 248 of the housing. Coding plate 246 is preferably a stiff coding plate and may comprise one or more coding features. In this particular arrangement, this coding plate 246 includes four coding features, 249-252. In this arrangement, the first two coding features 249 and 250 comprise plate protrusions and reside adjacent one another along a top surface of the plate. A third coding feature 251 comprises an aperture in the coding plate, and the fourth coding feature 252 adjacent the third coding feature 251 comprises yet another protrusion. Together, these four coding features may serve to identify a particular collapsible reservoir 240 containing a particular medicament. However, a coding plate arranged in a different way (e.g., all four coding features being a hole in the coding plate) may serve to identify a different reservoir containing a different medicament.

In an alternative arrangement, the collapsible drug reservoir may include a non-collapsible feature that is connected to the collapsible housing. In such an arrangement, the coding feature may be disposed on such a non-collapsible feature. Certain exemplary arrangements of possible coding features disposed along a non-collapsible feature of a collapsible reservoir are depicted in FIGS. 2(D)-(E).

As shown in FIG. 2(D), reservoir 260 includes collapsible housing 262 that is connected to non-collapsible portion 266. Non-collapsible portion 266 may be composed of various materials that result in a sturdy, non-collapsible structure. For instance, non-collapsible portion 266 may be composed of a polymer such as PP, acetal, PBT, COC, COP. This non-collapsible portion 266 may also include the fastening means to attach the reservoir 260 to a drug delivery device. This fastening means may be or may include the coding feature. For example, reservoir 260 includes coding feature 268, which are "T"-shaped protrusions from the reservoir. In such an example, coding feature 268 may slide into a corresponding groove in an intended drug delivery device. Other examples of non-collapsible coding features include a snap feature. Coding features disposed on a non-collapsible feature of the reservoir may fit into the device in any direction or combination of directions (e.g., axial, helical, and/or rotational directions).

FIG. 2(E) depicts another example of a non-collapsible coding feature of a collapsible reservoir 280. In this example, the port 284 of reservoir 280 includes a support ring 286, and this support ring 286 may be a stiff feature that prevents local collapse of the port 284. Further, the port 284 includes a plurality of coding features 288 which are indentations on the port 284. The port 284 may prevent reservoir 280 from being connected to an unintended drug delivery device by allowing the port 284 to only attach to a drug delivery device having a corresponding complimentary coding feature.

In additional embodiments, as mentioned above, the coding feature on a coded collapsible drug reservoir could be a coding feature that may be electronically detected. Reservoir 290 depicted in FIG. 2(F) includes such a coding feature. As shown, reservoir 290 includes a strip 296 of electronically detectable material disposed on the outer edge 298 of the reservoir 290. This material may be a conducting material such as copper that can be detected by interacting with an electrical circuit, or a polymer where the shape can be detected electronically, or a printed code that can be visually detected. This strip 296 of material may be detected by an electronic means as the reservoir 290 is inserted into a drug delivery device, or afterward the reservoir 290 is inserted into the device. Electronically detectable material 296 may be detected by any means now known in the art or later developed.

The collapsible housing may be formed in various ways. In addition, the collapsible housing may have a variety of shapes and sizes. For example, the collapsible housing may have a generally cylindrical shape, a generally oval shape, a generally triangular shape, or a generally trapezoidal shape. Other shapes and reservoir geometries are possible as well. Further, various examples of different shapes and sizes of collapsible housings and how to form such housings are discussed with reference to FIGS. 3(A)-(E).

Figure 3A:
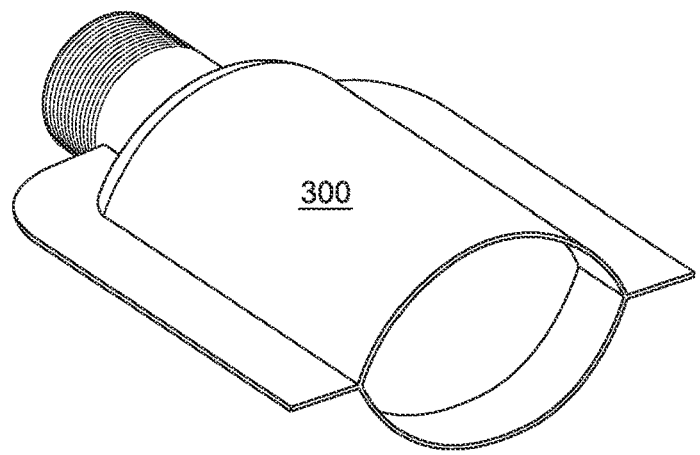
FIGS. 3(A)-(E) illustrate perspective views of examples of collapsible reservoirs, in accordance with exemplary embodiments.
Figure 3B:
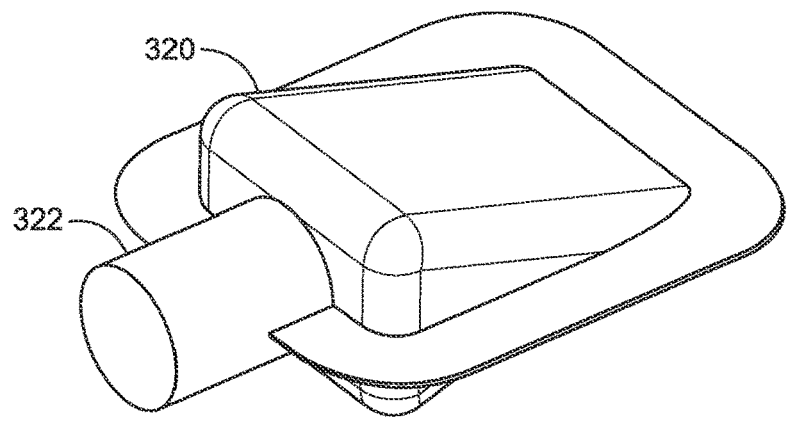
Figure 4A:
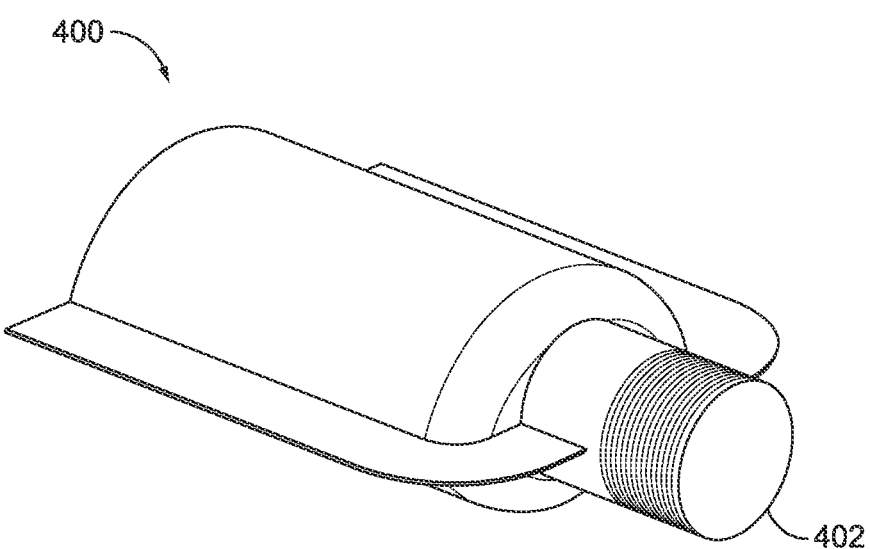
FIGS. 4(A)-(C) illustrate perspective views of examples of ports for collapsible drug reservoirs, in accordance with exemplary embodiments.

For example, FIG. 3(A) depicts a collapsible housing 300 that comprises a generally oval shape. Such a collapsible housing may be formed, for example, from a first sheet, a second sheet, and a third sheet material that are crimped together (i.e., sealed along their various edges). FIG. 3(B) depicts a collapsible housing 320 that comprises a generally triangular shape. Such a collapsible housing may be formed, for example, from two sheets of sheet material that are crimped together and taper away from the port 322 of the reservoir.

In other embodiments, the collapsible housing may be formed from a single sheet of sheet material. As just one example, FIG. 3(C) depicts a collapsible housing 340 that is formed from a single sheet that is folded at fold line 342 and then crimped together at the edges.

The shape and size of the coded collapsible drug reservoir may depend on the type of drug delivery device for which the reservoir is intended. For instance, FIG. 3(E) depicts a perspective cross-sectional view of a collapsible reservoir 380 that may be attached to a pen-type drug delivery mechanism.

Figure 4B:
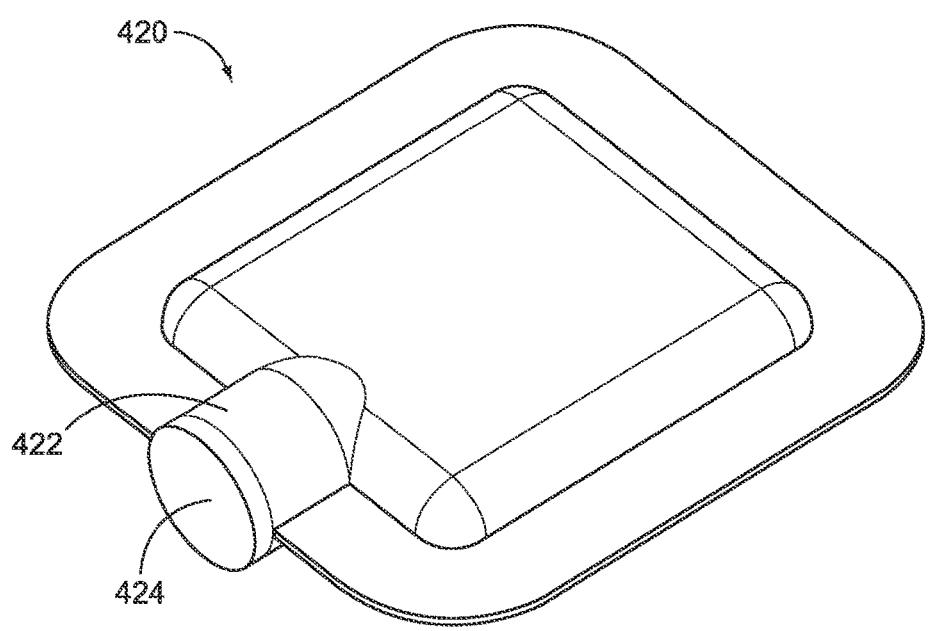
Figure 4C:
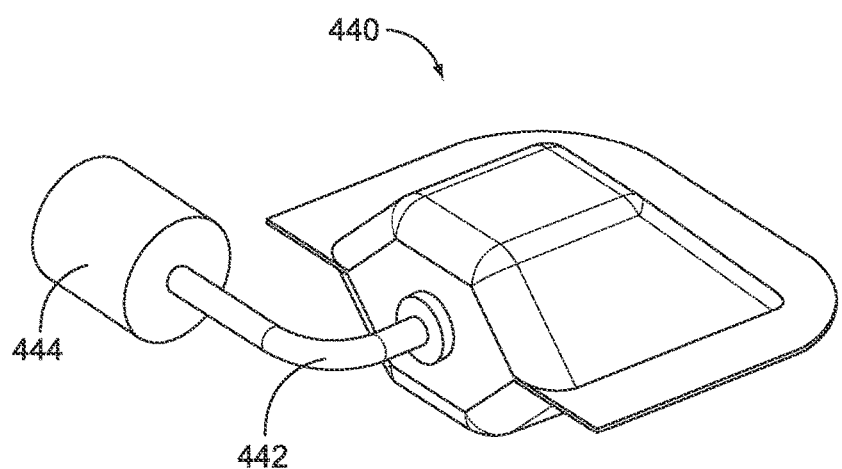

As described above, the coded collapsible reservoir may include a port that allows for the drug stored in the collapsible housing to exit the housing. This port may take various forms and may be different depending on the type of drug delivery device the reservoir is intended to be used with. For example, the port may include a hub for attaching a needle. For instance, with reference to FIG. 4(A), reservoir 400 includes port 402, which serves as a hub for attaching a needle assembly, such as a conventional double-ended needle assembly. As another example, the port may include only a septum. Such a reservoir 420 where the port 422 is only a septum 424 is depicted in FIG. 4(B). As yet another example, the port may include a tube that attaches to a needle hub. With reference to FIG. 4(C), reservoir 440 comprises a tube 442 that communicates with needle hub 444. Further, as mentioned above with reference to FIG. 2(E), the port may include a stiff feature (e.g., support ring 286) that may prevent local collapse of the port. The port may also include septum 289.

Figure 3C:
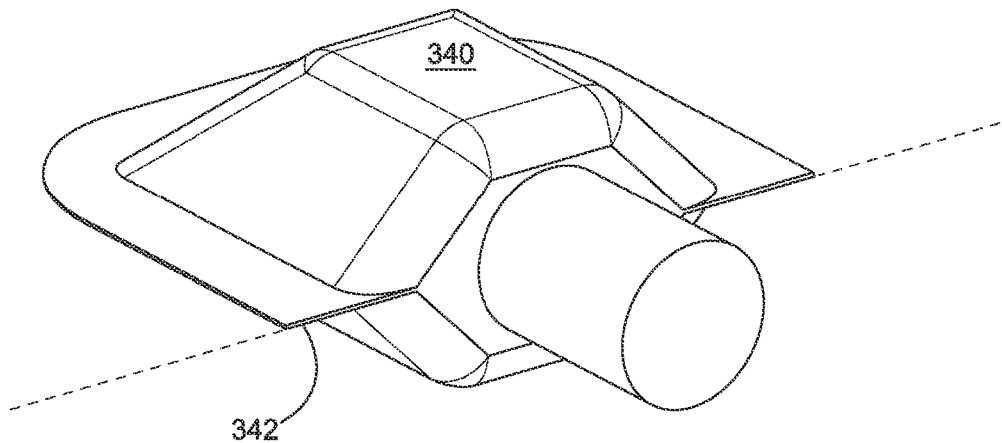
Figure 3D:
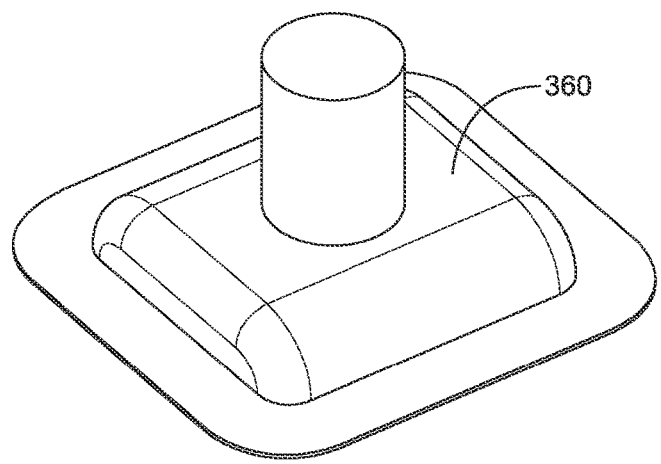
Figure 3E:
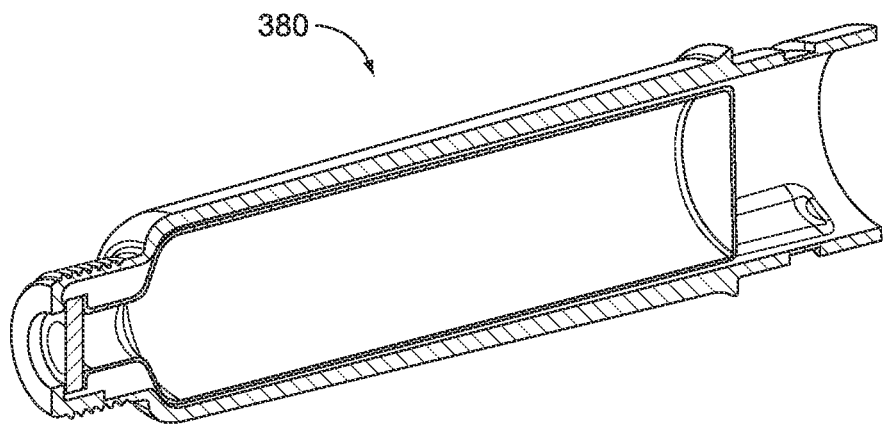

The port of the coded collapsible drug reservoir may be disposed on a sidewall of the reservoir, as shown in FIGS. 3(A)-(C). However, the port may be located elsewhere. For example, FIG. 3(D) depicts a collapsible housing 360 that includes a port attached to an upper-most face of the reservoir.

As mentioned above, the proposed coded collapsible drug reservoir may be used in conjunction with a suitable and intended drug delivery device. Accordingly, the drug delivery system to deliver medicament may comprise a housing containing a dose setter operably connected to a coded collapsible drug reservoir of medicament containing at least one drug agent. This reservoir is preferably the coded collapsible drug reservoir discussed above. The drug delivery system further includes a dose button operably connected to the reservoir of medicament, wherein the dose button may be capable of being depressed by a user of the drug delivery system.

The drug delivery system may further include a dispensing mechanism for dispensing medicament from the collapsible reservoir. This dispensing mechanism is preferably operably connected to the dose button and the reservoir. The dispensing mechanism preferably operates to dispense the medicament stored in the collapsible housing when a user compresses the dose button to deliver a dose. The dispensing mechanism may operate in various ways to compress the collapsible reservoir and, thus, force the medicament out through the port of the reservoir.

For example, the dispensing mechanism may use a suction force to dispense the drug. For instance, the dispensing mechanism may comprise a peristaltic pump acting on a tube. As another example, the dispensing mechanism may use a compression force to dispense the drug. For instance, the dispensing mechanism may comprise a screw mechanism that advances a platen or a roller, which may compress the collapsible reservoir and force medicament through the port. As yet another example, the dispensing mechanism may displace the collapsible housing by a sacrificial fluid. For instance, the coded collapsible drug reservoir may be placed in a non-collapsible housing, and liquid and/or gas may be pumped into the non-collapsible housing. This sacrificial fluid may compress the collapsible housing and thereby force medicament to flow out of the collapsible reservoir.

Other mechanisms for dispensing medicament from a collapsible reservoir are possible as well. For example, medicament may be dispensed from the proposed coded collapsible reservoirs by osmotic pressure or the force of gravity.

As mentioned above, the disclosed concepts result in a number of advantages. For example, as mentioned above, the coded collapsible reservoirs may be less expensive, more compact, and less fragile than typical standard drug reservoirs. Further, there are quite a large number of coding features that can be used. Consequently, with the disclosed coding features, a large number of medicaments can be distinguished from one another. Moreover, with the disclosed coded reservoirs, if a user attempts to load an incorrect reservoir, the user may be alerted at an early stage of assembling the reservoir into a delivery device that the user is attempting to load an incorrect reservoir, and hence attempting to possibly use a wrong medicament.

Exemplary embodiments of the present invention have been described. Those skilled in the art will understand, however, that changes and modifications may be made to these arrangements without departing from the true scope and spirit of the present invention, which is defined by the claims.

REFERENCE NUMERALS

100 Drug delivery device
102 Reservoir retaining part/cartridge holder
104 Main housing part
106 Retaining feature
110 Dose setting mechanism
112 Dose button
200 Collapsible drug reservoir
202 Collapsible housing
204 Port
206 Coding feature
208 Coding feature
210 Coding feature
212 First outer edge
214 Second outer edge
220 Collapsible drug reservoir
222 Collapsible housing
224 Port
226 Coding feature
228 Coding feature
230 Coding feature
240 Collapsible drug reservoir
242 Collapsible housing
244 Port
246 Coding plate
248 Outer edge
249 Coding feature
250 Coding feature
251 Coding feature
252 Coding feature
260 Collapsible drug reservoir
262 Collapsible housing
264 Port
266 Non-collapsible portion
268 Coding feature
280 Collapsible drug reservoir
282 Collapsible housing
284 Port
286 Stiff feature/support ring
288 Coding feature
289 Septum
290 Reservoir
292 Collapsible housing
294 Port
296 Strip
298 Outer edge
300 Collapsible housing
320 Collapsible housing
322 Port
340 Collapsible housing
342 Fold line
360 Collapsible housing
380 Reservoir
400 Reservoir
402 Port
420 Reservoir
422 Port
424 Septum
440 Reservoir
442 Tube
444 Needle hub

The invention claimed is:

1. A drug reservoir which is adapted for use with a drug delivery device, the drug reservoir comprising:
a collapsible housing;
a coding feature; and
a non-collapsible feature connected to the collapsible housing,
wherein the non-collapsible feature comprises the coding feature,
wherein the coding feature is arranged on an outer edge of the drug reservoir,
wherein said coding feature is configured to code information related to the drug reservoir, the coding feature comprising a mechanical coding feature which is configured to cooperate with a corresponding coding feature provided by the drug delivery device, and
wherein a mechanical cooperation of the coding feature and the corresponding coding feature of the drug delivery device helps to prevent insertion of a reservoir having a wrong coding feature into the drug delivery device, the coding feature comprising at least one of an embossed feature, a hole or an indentation of the drug reservoir.

2. The drug reservoir of claim 1, wherein the collapsible housing contains a medicament having at least one drug agent.

3. The drug reservoir according to claim 1, wherein the coding feature is configured to be electronically detectable.

4. The drug reservoir according to claim 1, wherein the outer edge comprises a sealing means of the drug reservoir.

5. The drug reservoir according to claim 1, wherein the drug reservoir comprises a port which is adapted and arranged for fluid communication with the collapsible housing.

6. The drug reservoir according to claim 5, wherein the port comprises a needle hub for attaching a needle or a septum to the drug reservoir.

7. The drug reservoir according to claim 1, wherein the collapsible housing comprises a plurality of sheets of a sheet material adapted to form the collapsible housing, and wherein the plurality of sheets are sealed together.

8. The drug reservoir according to claim 1, wherein the collapsible housing is constructed from a single sheet of a sheet material that is folded and crimped together to form the collapsible housing.

9. The drug reservoir according to claim 1, wherein a shape of the drug reservoir is configured to act as the coding feature.

10. The drug reservoir according to claim 1, wherein the collapsible housing comprises one of the following structures:
    a generally cylindrical structure,
    a generally oval-shaped structure,
    a triangular-shaped structure, or
    a trapezoidal-shaped top surface.

11. A drug delivery system which is configured to deliver a medicament, comprising a housing which is configured to receive the drug reservoir according to claim 1.

12. The drug delivery system of claim 11, further comprising a dispensing mechanism configured for dispensing the medicament from the drug reservoir, wherein the dispensing mechanism provides at least one of a suction force, a compression force, or a sacrificial fluid in order to dispense the medicament from the drug reservoir.

13. The drug delivery system of claim 11 further comprising the corresponding coding feature provided by the drug delivery device, the corresponding coding feature being adapted and arranged to cooperate with the coding feature of the drug reservoir when the drug reservoir is connected to the drug delivery system.

14. The drug delivery system of claim 13, wherein a cooperation of the coding feature of the drug reservoir and the corresponding coding feature provided by the drug delivery device is configured to prevent a use of the drug delivery system with the reservoir having the wrong coding feature.

15. The drug reservoir of claim 1, wherein the non-collapsible feature comprises a fastener configured to couple the drug reservoir to the drug delivery device.

16. The drug reservoir according to claim 1, wherein the outer edge of the drug reservoir is an edge of the collapsible housing.

17. A drug reservoir which is adapted for use with a drug delivery device, the drug reservoir comprising:
    a collapsible housing; and
    a first coding feature configured to code information related to the drug reservoir,
    wherein the first coding feature is arranged on an outer edge of the drug reservoir,
    wherein the first coding feature is configured to mechanically mate with a second coding feature of the drug delivery device when the drug reservoir is inserted into the drug delivery device,
    wherein the first coding feature is configured to prevent the drug reservoir from being fully inserted into a second drug delivery device having a third coding feature due to a non-mating between the first coding feature of the drug reservoir and the third coding feature of the second drug delivery device.

18. The drug reservoir of claim 17, wherein the first coding feature comprises at least one of an embossed feature, a hole or an indentation of the drug reservoir.

19. The drug reservoir of claim 17, wherein the first coding feature comprises at least one of an indentation or a protrusion.

20. A drug reservoir which is adapted for use with a drug delivery device, the drug reservoir comprising:
    a collapsible housing;
    a coding feature; and
    a non-collapsible feature connected to the collapsible housing,
    wherein the non-collapsible feature comprises the coding feature,
    wherein the coding feature is arranged on an outer edge of the drug reservoir,
    wherein said coding feature is configured to code information related to the drug reservoir and is configured to be electronically detectable, and
    wherein electronic detection of the coding feature allows use of the drug reservoir in the drug delivery device and failure of the drug delivery device to electronically detect the coding feature prevents dispensing from the drug delivery device.

* * * * *